United States Patent [19]

Oyama et al.

[11] Patent Number: 5,444,173
[45] Date of Patent: Aug. 22, 1995

[54] CATALYTIC BIMETALLIC OXYNITRIDES AND NITRIDES

[75] Inventors: Shigeo T. Oyama; Chunzhe C. Yu, both of Blacksburg, Va.; Fawzy G. Sherif, Stony Point, N.Y.

[73] Assignees: Akzo Nobel N.V., Arnhem, Netherlands; Clarkson University, Potsdam, N.Y.

[21] Appl. No.: 155,420

[22] Filed: Nov. 19, 1993

[51] Int. Cl.$^6$ ............... B01J 27/24; C07C 5/22
[52] U.S. Cl. ............... 585/671; 502/200; 208/112; 585/670; 585/750; 423/351; 423/385
[58] Field of Search ........... 502/200; 423/351, 385; 585/671, 670, 750; 208/112

[56] References Cited

U.S. PATENT DOCUMENTS

| | | | |
|---|---|---|---|
| 4,325,843 | 4/1982 | Slaugh et al. | 252/443 |
| 4,326,992 | 4/1982 | Slaugh et al. | 252/443 |
| 4,414,182 | 11/1983 | Okamoto et al. | 423/652 |
| 4,426,366 | 1/1984 | McCandlish et al. | 423/365 |
| 4,977,125 | 12/1990 | Lednor | 502/200 |
| 5,071,813 | 12/1991 | Kugler et al. | 502/200 |
| 5,138,111 | 8/1992 | Kugler et al. | 585/277 |
| 5,188,908 | 2/1993 | Nishiyama et al. | 428/698 |
| 5,200,600 | 4/1993 | Sajkowski et al. | 208/108 |

OTHER PUBLICATIONS

P. Duwez et al., J. Electrochem. Soc., 97, 299–304 (1950).
N. Schönberg, Acta Met., 2, 427–432 (1954).
Naturwissenschaften, 41, 117 (1954).
N. Schoönberg, Acta Chemica Scandinavica, 8, 213 (1954).
D. A. Evans et al., Acta Cryst., 10, 769–770 (1957).
R. Juza et al., Z. Elektrochem., 63, 551–557 (1959).
W. Jeitschko et al., Monatsch. Chem., 94, 1198–1200 (1963).
W. Jeitschko et al., Monatsch. Chem., 95, 156–157 (1964).
H. Nowotny et al., Phase Stability in Metals and Alkyls (McGraw Hill, 1967) pp. 319–336.
Catalysis Today, 15 (1992) 179–200.
Catalysis Today, 15 (1992) 243–261.
W. Jeitschko et al., Monatsch. Chem. 95, 178–179 (1964).
T. Yamamoto et al., Solid State Ionics 63–65 (1993) 148–153.
D. S. Bem et al., Journal of Solid State Chemistry 104, 467–469 (1993).

*Primary Examiner*—Asok Pal
*Attorney, Agent, or Firm*—Richard P. Fennelly; Louis A. Morris

[57] ABSTRACT

Bimetallic oxynitrides and nitrides which have catalytic properties comprise two transition metals selected from Groups IIIB to VIII of the Periodic Table of the Elements. Preferably, one metal is either molybdenum or tungsten. The other can be tungsten or molybdenum, respectively, or another transition metal, such as vanadium, niobium, chromium, manganese, cobalt, or nickel. They have a face centered cubic (fcc) arrangement of the metal atoms and have a surface area of no less than about 40 m$^2$/gm.

25 Claims, No Drawings

CATALYTIC BIMETALLIC OXYNITRIDES AND NITRIDES

BACKGROUND OF THE INVENTION

Various disclosures exist in the art concerning compositions comprising at least one transition metal in carbide/nitride form. A recent review article in this area, which shows both single metal and bimetallic carbides and nitrides, is S. T. Oyama, "Preparation and Catalytic Properties of Transition Metal Carbides and Nitrides", Catalysis Today, 15 (1992), 172–200. The bimetallic species listed on page 183 in Table 4 are carbides, nitrides, and carbonitrides but the listing is based on R. B. Kotel'nikov, Zhur. Neorg. Khim., 3 (1958) 841 in which no experimental data is provided. Bimetallic nitrides which are known to have B1 phases (P. Duwez et al., J. Electrochem. Soc. (1950) 97, 299), hexagonal phases (N. Schönberg, Acta Chem. Scand. (1954) 8, 213 and Acta Med. (1954), 2,427), Perovskite phases (R. Juza et al., Z. Elektrochem. Soc. (1959), 63, 551), $\beta$—Mn phases (D. A. Evans et al., Acta Cryst. (1957), 10, 769), H— phases (W. Jeitschko et al., Monatsh. Chem. 94, 95 and 95, respectively (1963, 1964 and 1964, respectively), 1198, 156, and 178, respectively), and eta-carbide phases (H. Nowotny et al., in "Phase Stability in Metals and Alloys", P. S. Rudman et al., ed., 1967, New York, p. 319 and U.S. Pat. No. 5,138,111 to E. L. Kugler et al.). The bimetallic nitrides synthesized by P. Duwez and co-workers were prepared isothermally at very high temperatures (e.g., 2398° K. or higher) and would have surface areas in the neighborhood of 1 ma/gm or less.

Representative disclosures of single metal carbides or nitrides having catalytic properties include the following: U.S. Pat. Nos. 4,325,843 and 4,326,992 to L. H. Slaugh et al. (supported tungsten carbide and molybdenum carbide compositions); and U.S. Pat. No. 5,200,060 to D. J. Sajkowski et al. (Group VIB metal carbide or nitride compositions). U.S. Pat. No. 4,426,366 to L. E. McCandlish deals with the single metal molybdenum oxycarbonitride compositions.

U.S. Pat. No. 5,188,908 to A. Nishijama et al. describes an alumina-based ceramic which contains a hard dispersed phase which comprises a metal carbide, metal nitride, metal carbo-nitride, metal oxy-carbide, metal oxynitride or metal carbo-oxy-nitride. The metal may be at least one metal selected from the group consisting of titanium, zirconium, and hafnium. The monometallic composition $TiN_{0.9}O_{0.1}$ is shown in Table 1–1a, No. 9, one of the "M(CNO)" powders that were blended.

SUMMARY OF THE INVENTION

The present invention relates to novel oxynitride compositions which comprise two different transition metals. These bimetallic oxynitrides preferably contain at least one metal selected from the group consisting of molybdenum and tungsten. The other metal can be tungsten and molybdenum, respectively, or another transition metal from Groups IIIB to VIII of the Periodic Table of the Elements. Some salient features of this invention are products that have a metal face centered cubic (fcc) structure, that have high surface areas, and, in the case of the oxynitrides, that are produced at relatively low temperatures with short nitriding times. The present invention also relates to novel bimetallic nitrides, containing the aforementioned metal components, where the metal atoms are in a novel face centered cubic (fcc) arrangement and which have a surface area of not less than about 40 m²/gm.

DESCRIPTION OF DETAILED EMBODIMENTS

The novel bimetallic oxynitrides of the present invention have the general formula

$$M_I M_{II} NO$$

with $M_I$ and $M_{II}$ each being a transition metal from Groups IIIB to VIII of the Periodic Table of the Elements. If the above general formula is examined for the relative molar amounts of the respective elements, the following relationships pertain: The ratio of $M_I$ to $M_{II}$ will vary from about 1:3 to about 3:1. Since the radii of nitrogen and oxygen are close, oxygen substitutes for nitrogen in the known nitrides without changing the crystal structure. The resulting X-ray diffraction (XRD) patterns show face centered cubic (fcc) structures with lattice parameters distinct from the pure single nitrides and structures completely different from the starting oxides.

Preferred oxynitrides contain either molybdenum or tungsten as one of the metals, with the other being another transition metal from Groups IIIB-VIII of the Periodic Table of the Elements. If desired, the other metal can be tungsten or molybdenum, respectively. Representative other metals for selection include: yttrium (Group IIIB); vanadium or niobium (Group VB); chromium (Group VIB); manganese (Group VIIB) and; cobalt or nickel (Group VIII).

The oxynitrides can be prepared by the temperature programmed reduction of double oxides of the selected metals under a nitriding gas such as ammonia. The double oxides are preferably prepared from the corresponding single oxides by solid state reaction or fusion techniques. This, however, does not preclude the use of other methods like coprecipitation or spray drying or sol-gel processing for producing the double oxide precursors. The following U.S. patents, which are each incorporated herein by reference, illustrate the temperature programmed reduction of mixed metal oxides as used to form carbides and nitrides: U.S. Pat. Nos. 4,515,763 and 4,851,206 to M. Boudart et al. These conventional processes are modified to form the instant bimetallic oxynitrides by lowering the temperature and shortening the processing time. The preferred heating rate is 5° C. per minute and the preferred ammonia flow rate is 1000 cc per minute, but other conditions can be employed. With use of such conditions with single phase bimetallic oxides (also termed "double oxides") as precursors, the following potential problems can be largely avoided: preferential reduction of one metal component which can lead to phase separation in the initial stage of reaction; over-reduction leading to the occurrence of a free metal phase in the final product; and preferential nitridation which also leads to phase separation.

The bimetallic oxynitrides of the present invention possess catalytic activity, for example, in hydrotreating processes, and have a number of interesting characteristics. They are stable, with high surface areas (generally in the range of about 40 m²/gm to 125 m²/gm), and have a B1 cubic crystal structure (rock salt), where the metal atoms are placed in a face-centered cubic (fcc) arrangement with nitrogen or oxygen filling each octahedral interstitial position. They have a substantial nitrogen and (in the case of the oxynitrides) oxygen content (e.g., nitrogen: 5-15 wt %; oxygen: up to 25 wt %). The oxygen content can be controlled by varying the nitridation time. Longer times result in more complete removal of the oxygen as demonstrated in Example 1, below. Indeed, the resulting nitrides produced from such longer nitriding times are deemed to be novel over known bimetallic nitrides in regard to their higher surface area and the face centered cubic (fcc) arrangement of the metal atoms therein. The diffraction peaks for such materials are unusually broad, indicating a finely divided substance. The crystallite size ($D_c$), as calculated by the Scherrer equation (P. Scherrer, Gött. Nachr. 1918, 2, 98) indicates dimensions of from about 3 to about 11 nm which is confirmed by the aforementioned high values for surface area ($S_g$). The particle size can be calculated from the equation $D_p = 6/S_g \rho$, where $\rho$ is taken to be 10.2 g/cm$^3$ for molybdenum oxynitride compounds and 18.9 g/cm$^3$ for tungsten oxynitride compounds, assuming a substantially perfect B1 structure for such compounds. Good agreement exists for $D_p$ and $D_c$.

The instant materials chemisorb carbon monoxide in the range of from 0.01 to $0.10 \times 10^{15}$ cm$^{-2}$ which indicates that only from about 1%-10% of the surface metal atoms are chemisorbing carbon monoxide.

It is envisioned that the catalysts described herein can be employed in hydrotreating processes in which a hydrocarbon feedstock is treated at elevated temperature (e.g., 350° C.-400° C.) and under pressure (e.g., up to about 1000 psig). They can also be used in a hydroisomerization process under similar conditions with a hydrocarbon feedstock.

The present invention is further understood by reference to the Examples which follow.

EXAMPLE 1

This Example illustrates the general procedure used hereinafter in forming a precursor for the bimetallic oxynitrides of the present invention.

A vanadium-molybdenum double oxide was prepared by solid state fusion of vanadium pentoxide ($V_2O_5$, 99.9%, Johnson Matthey) and molybdenum trioxide ($MoO_3$, 99.95%, Johnson Matthey). Vanadium pentoxide ($V_2O_5$) and $MoO_3$ were first mixed, at a V:Mo metal ratio of 2:1, using a mortar and pestle. Ethanol was added during the grinding for better dispersion. After mixing, the mixture was partially dried and was then pressed at about 8,000 psi in a one-half inch diameter hard steel die. Since the remaining ethanol in the mixture facilitated compacting, no binder was needed for pellet pressing. The oxide mixture pellets were then fired at 948° K. for six hours. After cooling down to room temperature, the product was pulverized. The X-ray diffraction analysis confirmed the formation of a double oxide.

The vanadium-molybdenum double oxide powders thus obtained were then transferred to a quartz reactor, which was then placed inside a tubular resistance furnace. An ammonia gas stream was passed through the oxide sample at a flow rate of 1000 cm$^3$/min, and the temperature was increased at a heating rate of 5° K./min. Upon reaching 1020° K., the reactor was held at that temperature for twenty minutes, then ammonia was switched to helium, and the reactor was quenched to room temperature by simply removing the furnace. The flow of helium gas was continued through the reactor for about fifteen minutes in order to completely cool the sample. After cooling, the pure helium gas was switched to a gas mixture containing 0.5% oxygen in helium at a flow rate of 35 cm$^3$/min to passivate the sample. The time of passivation was set for three hours per gram of starting double oxide. Elemental analysis of the product showed it to have a composition of $V_{2.1}Mo_{1.0}O_{4.0}N_{2.3}$. Another sample prepared in an identical manner but nitrided at 1040° K. for thirty minutes has a composition of $V_{2.0}Mo_{1.0}O_{1.7}N_{2.4}$.

EXAMPLES 2-21

The general process of Example 1 was followed using different starting monometallic oxides and acetates: $Y_2O_3$ (99.99%, Johnson Matthey); $Nb_2O_5$ (99.9%, Johnson Matthey); $CrO_3$ (99.5%, Johnson Matthey); $Mn_3O_4$ (Johnson Matthey); $COC_2H_6O_4$ (Aldrich), $Co_3O_4$ (Aldrich); and $WO_3$ (99.8%, Johnson Matthey). The differences in processing conditions are noted in Table 1 and Table 2 which follow:

TABLE 1

Preparation Conditions for Oxide Precursors

| System ($M_I$-$M_{II}$) | Starting Materials | Metal Ratio ($M_I$:$M_{II}$) | Firing Temp. ($T_{MAX}$) (K) | Time Hold at $T_{MAX}$ (Hours) |
|---|---|---|---|---|
| Y—Mo | $Y_2O_3$—$MoO_3$ | 1:1 | 1273 | 6 |
| V—Mo | $V_2O_5$—$MoO_3$ | 2:1 | 948 | 6 |
| Nb—Mo | $Nb_2O_5$—$MoO_3$ | 2:3 | 1058 | 6 |
| Cr—Mo | $CrO_3$—$MoO_3$ | 1:1 | 1058 | 6 |
| Mn—Mo | $Mn_3O_4$—$MoO_3$ | 1:1 | 1013 | 6 |
| Co—Mo | $CoC_2H_6O_4$—$MoO_3$ | 1:1 | 1058 | 6 |
| Ni—Mo | NiO—$MoO_3$ | 1:1 | 1058 | 6 |
| V—W | $V_2O_5$—$WO_3$ | 1:1 | 1323 | 6 |
| Nb—W | $Nb_2O_5$—$WO_3$ | 2:3 | 1323 | 6 |
| Mo—W | $MoO_3$—$WO_3$ | 1:1 | 1058 | 6 |
| Co—W | $Co_3O_4$—$WO_3$ | 1:1 | 1370 | 6 |

TABLE 2

Synthesis Conditions for Bimetallic Nitrides/Oxynitrides

| System ($M_I$-$M_{II}$) | Metal Ratio ($M_I$:$M_{II}$) | Firing Temp. ($T_{MAX}$) (K) | Time Hold at $T_{MAX}$ (Minutes) |
|---|---|---|---|
| Y—Mo—O—N | 1:1 | 1023 | 60 |
| V—Mo—O—N | 2:1 | 1037 | 30 |
| Nb—Mo—O—N | 2:3 | 1063 | 20 |
| Cr—Mo—O—N | 1:1 | 1013 | 20 |
| Mn—Mo—O—N | 1:1 | 935 | 36 |
| Co—Mo—O—N | 1:1 | 892 | 20 |
| Ni—Mo—O—N | 1:1 | 986 | 20 |
| V—W—O—N | 1:1 | 1009 | 110 |
| Nb—W—O—N | 2:3 | 1113 | 20 |
| Mo—W—O—N | 1:1 | 991 | 20 |
| Co—W—O—N | 1:1 | 1063 | 24 |

Heating rate = 5 K/min.
Ammonia flow rate = 1000 cm$^3$/min.

The chemical analysis of the above binary oxynitrides possessed the compositions as shown in Table 3 which follows.

TABLE 3

Molar Composition of Bimetallic Oxynitrides $M^I_wM^{II}_xO_yN_z$ (from Elemental Analysis)

| Sample | $M^I:M^{II}$ (Theoretical) | V | Nb | Cr | Mn | Co | Mo | W | O | N |
|---|---|---|---|---|---|---|---|---|---|---|
| V—Mo—O—N | 2:1 | 2.0 | | | | | 1.0 | | 1.7 | 2.4 |
| Nb—Mo—O—N | 2:3 | | 2.0 | | | | 2.6 | | 3.0 | 4.2 |
| Cr—Mo—O—N | 1:1 | | | 1.0 | | | 1.3 | | 2.3 | 1.4 |
| Mn—Mo—O—N | 1:1 | | | | 1.0 | | 1.0 | | 1.5 | 0.88 |
| Co—Mo—O—N | 1:1 | | | | | 1.0 | 1.0 | | 1.6 | 0.79 |
| Nb—W—O—N | 2:3 | | 2.0 | | | | | 2.8 | 4.5 | 5.1 |
| V—W—O—N | 1:1 | 1.0 | | | | | | 1.4 | 2.7 | 2.5 |
| Mo—W—O—N | 1:1 | | | | | | 1.0 | 1.0 | 2.4 | 2.1 |
| Co—W—O—N | 1:1 | | | | | 1.0 | | 1.0 | 1.2 | 1.0 |

EXAMPLES 24–31

These Examples illustrate the characterization of selected bimetallic oxynitrides from the previous Examples.

X-ray diffraction (XRD) analysis of the bimetallic oxynitrides was carried out using a powder diffractometer (Siemens, Model D 500 with a CuKα monochromatized radiation source), operated at 40 kV and 30 mA. Elemental analysis of the sample was carried out by Inductively Coupled Plasma (ICP). The sample was also characterized by sequential temperature programmed reduction (TPR) to 738° K., CO chemisorption, $N_2$ physisorption and a final TPR to 1373° K.

Approximately 0.2 gram of the bimetallic oxynitride samples were loaded into a quartz micro-reactor, which was then placed inside the tubular resistance furnace. A 10% $H_2$ in He gas mixture was passed through the sample at a rate of 20.4 μmol sec$^{-1}$ (30 cm$^3$/min). The temperature was increased at a linear rate of 0.16 Ks$^{-1}$ (10° K./min) to 738° K., where it was held for two hours. The temperature of the sample was measured through a Chromel-Alumel type thermocouple placed in a well located at the center of the reactor bed. During the temperature programmed reaction (TPR) process, the effluent gas stream was sampled into a mass spectrometer (Ametek/Dycor Model MA100) through a variable leak valve (Granville Phillips Model 203). A computer (Thoroughbred, 80386SX-16) recorded the mass signals of the effluent gas and the sample temperatures through a RS232 interface. At the end of the TPR process, the $H_2$/He gas mixture was switched to pure He, and the samples were brought to room temperature for CO chemisorption measurements.

Carbon monoxide chemisorption was used to titrate the surface metal atoms in the sample. After the two hour reduction described above, pulses of CO gas were introduced through a sampling valve with the He carrier gas stream passing over the samples. The total uptake was calculated by referring the areas under the CO mass signal (28) peaks to the known quantity of 12.02 μmol CO for a single peak.

Surface areas were determined immediately after the CO uptake measurements by a similar flow technique using a 30% $N_2$ in He gas mixture passed over the samples maintained at liquid nitrogen temperature. The amount of physisorbed $N_2$ was obtained by comparing the area of the desorption peaks to the area of calibrated $N_2$ pulses containing 37.95 μmol $N_2$/pulse. The surface area was then calculated from the single point BET equation.

The final TPR to 1373° K. was carried out on the same samples which had undergone CO chemisorption in the same manner as the initial TPR. During the TPR process, the mass signals of the effluent gases as well as the sample temperature were again recorded.

TABLE 4

Characteristics of Bimetallic Oxynitrides

| Compounds | CO uptake (μmol g$^{-1}$) | Surface Area ($S_g$ m$^2$ g$^{-1}$) | Site Density ($\times 10^{15}$ cm$^{-2}$) | Particle Size $D_p$ (nm) | Crystallite Size $D_c$ (nm) |
|---|---|---|---|---|---|
| V—Mo—O—N | 138 | 78 | 0.11 | 7.5 | 11 |
| Cr—Mo—O—N | 163 | 90 | 0.11 | 6.6 | 3.9 |
| Co—Mo—O—N | 186 | 103 | 0.11 | 5.7 | 4.5 |
| Mo—W—O—N | 59.8 | 118 | 0.031 | 5.0 | 6.5 |
| Co—W—O—N | 12.5 | 45 | 0.017 | 7.1 | 3.8 |
| Mn—Mo—O—N | 10.6 | 37 | 0.017 | 15.8 | 3.5 |
| V—W—O—N | 9.67 | 62 | 0.0094 | 5.1 | 6.7 |
| Nb—Mo—O—N | 11.2 | 121 | 0.0056 | 4.9 | 5.3 |

$D_p = \dfrac{6}{S_g \rho}$ $\rho_{Mo} = 10.2$ g cm$^{-3}$ $\rho_W = 18.9$ g cm$^{-3}$ $D_c = \dfrac{K\lambda}{\beta \cos\theta}$ $\beta^2 = B^2 - b^2 = B^2 - 0.1^2$

EXAMPLES 32–42

These Examples provide a summary of the catalytic testing of several known catalysts, certain transition metal carbides and nitrides, and a vanadium-molybdenum-oxynitride in accordance with this invention.

Catalysts were evaluated in a three-phase, trickle-bed reactor system operated at 450 psig (3.1 MPa) and 350°–400° C. The system consisted of three parallel reactors immersed in a heated fluidized sand bath (Techne Model 2BL-2) controlled by a relayed temperature controller (Omega 6051K). The reactors were of 19 mm/16 mm outer diameter/inner diameter (OD/ID) with a central thermocouple well and were made of 316 stainless steel. Catalysts were in the form of coarse powders or pellets sieved to 16/20 mesh (1.00–0.841 mm), and were held in 13 mm OD 1 cm³ beds.

Hydrogen purified through an $O_2$-$H_2O$ trap (Supelco OMI-1 lithium resin) was brought to high pressure by an air driven compressor (Autoclave Engineers Gas Booster Model DLE 15-75) in a closed loop equipped with a back pressure regulator (GO, Inc. BP-60). Gases were drawn through forward pressure regulators (GO, Inc. PR-50) to mass flow controllers (Brooks Model 5850E), while the liquid feed mixture was metered from burettes by high pressure liquid pumps (LDL Analytical Model NCI-1105) into the gas lines. The reactant mixture was passed in up-flow mode through the catalyst bed and out to the collecting system. The gas/liquid mixture was separated by gravity in a first vessel, which also served to hold the liquid for intermittent injection into sealed septum bottles. Excess liquid was stored in a second pressurized vessel. The gases were passed through back pressure regulators for control of the total reactor pressure, through a sampling valve for gas chromatographic (GC) (Hewlett Packard Model 5890) analysis, and out to vent.

Separate GC analysis was carried out for the gases and the liquids. The gases were analyzed in-line using a Hayesep Q80/100 mesh column (Alltech) and a thermal conductivity detector. The liquids were analyzed off-line using a CPSIL 5CB fused silica capillary column (Chrompak) and a flame ionization detector. The liquid-phase reactant mixture consisted of 3000 ppm as sulfur (dibenzothiophene, DBT), 2000 ppm as nitrogen (quinoline, QNL), 500 ppm as oxygen (benzofuran, BZF), 20 wt % aromatics (tetralin, TTL) and balance aliphatics (tetradecane, TTD). The liquid-phase mixture was fed at a liquid feed rate of 5 cm³/h. Gas feed was 150 cm³/min (100 $\mu$mol s$^{-1}$) which gave an equivalent flow of 9800 SCF/barrel. The reactant mixture was composed of sulfur, nitrogen, oxygen and aromatic compounds, all of different carbon number. Thus, it was possible to carry out a one-column analysis of all the reactants and products of reaction. The conversions of each reactant were defined in terms of the fraction of each compound that reacted.

The performance of the Ni-Mo/$Al_2O_3$ (Shell 324) and the Co-Mo-$Al_2O_3$ (Ketjenfine 752) were used as references for comparison. The $Mo_2C$, WC and $Mo_2N$ samples were the initial samples tested.

The most substantive result was obtained by the V-Mo-O-N compound. It showed very good stability over sixty hours of reaction time. It was lower in HDS than the commercial Shell 324 catalyst, but was higher in HDN. Importantly, it performed better than VN at the same condition (370° C.) and $Mo_2N$ at 400° C. This indicates that compound formation is beneficial for stability and activity.

TABLE 5

Summary of Catalyst Performance in Hydrotreating Process

| Catalyst | Temperature °C. | Pressure psig | HYD % | HDN % | HDS % | HDO % | LHSV h$^{-1}$ | Spacetime 10³/cm³g$^{-1}$s$^{-1}$ | Gas/Liquid SCF/barrel |
|---|---|---|---|---|---|---|---|---|---|
| Shell 324 | 350 | 450 | 58 | 35 | 75 | 52 | 5 | 4.6 | 9800 |
| Shell 324 | 370 | 450 | 47 | 38 | 79 | 63 | 5 | 3.8 | 9800 |
| Shell 324 | 400 | 450 | 35 | 22 | 80 | 60 | 5 | 4.6 | 9800 |
| Ketjenfine (752-1.3Q) | 350 | 450 | 32 | 63 | 89 | 75 | 7 | 1.9 | 10700 |
| WC$^{(1)}$ | 350 | 450 | 53 | 32 | 7 | — | 11.2 | 1.7 | 9800 |
| WC$^{(2)}$ | 350 | 450 | 67 | 11 | 21 | 51 | 11.2 | 1.7 | 9800 |
| $Mo_2C^{(1)}$ | 350 | 450 | 35 | 55 | 35 | 35 | 5 | 1.4 | 9800 |
| $Mo_2C^{(1)}$ | 400 | 450 | 36 | 5 | 30 | 26 | 5 | 1.4 | 9800 |
| $Mo_2N$ | 370 | 450 | 50 | 22 | 18 | 15 | 5 | 3.5 | 9800 |
| VN | 370 | 450 | 63 | 2 | 6 | 44 | 5 | 1.5 | 9800 |
| V—Mo—O—N | 370 | 450 | 44 | 45 | 25 | 28 | 5 | 1.8 | 9800 |

HYD = hydrogenation.
HDN = hydrodenitrogenation.
HDS = hydrodesulfurization.
HDO = hydrodeoxygenation.
LHSV = liquid hourly space velocity.
$^{(1)}$: carbides were prepared by methane carburization of the oxides.
$^{(2)}$: carbide was prepared by reaction of tungsten hexachloride and guanidine hydrochloride followed by heating.

EXAMPLE 43

This Example illustrates the catalytic performance in the isomerization of n-heptane with hydrogen of the vanadium-molybdenum nitride-oxynitride. This was a different sample from that reported in Table 2, above. It was prepared in a similar fashion but was more severely surface oxidized during passivation. It had a chemical formula $V_{2.1}Mo_1N_{2.3}O_{4.0}$. This material had the following physical properties:

$S_A$ = 110 m²/g
CO up-take = 100 $\mu$mol/g
Elemental analysis: (Wt %)
  V   Mo   N   (O)
  36   32   10.8  21.2
Lattice parameter (fcc): a = 4.13
$\gamma$-$Mo_2N$ (fcc): a = 4.16
$VN_x$ (fcc):  a = 4.07   a = 4.14
          (x = 0.72)  (x = 1.00)
a($VN_x$) < a(V-Mo-1) < a($\gamma$-$Mo_2N$)

The catalyst was preactivated with hydrogen at 500° C. for sixteen hours before use. The isomerization was performed in an 8 mm diameter reactor using 0.5 gram of catalyst with a flow rate of 10 cm³/minute of hydrogen which was saturated with n-heptane at 25° C. The results were:

| Reaction Temp (°C.) | Conversion (%) | Selectivity | | Aromatics (%) |
| | | $C_6$–$C_7$ Isomers (%) | $C_1$–$C_6$ Hydrocarbons (%) | |
|---|---|---|---|---|
| 350 | 1 | 44.8 | 29.5 | — |
| 400 | 11 | 26.4 | 66.4 | 2.6 |
| 450 | 30 | 14.0 | 49.8 | 10.5 |
| 500 | 39 | 9.7 | 46.1 | 35.6 |

Conversion to $C_6$ and $C_7$ isomers and to aromatics was achieved.

EXAMPLE 44

The same procedure used in Example 43 was used with the niobium-tungsten nitride-oxynitride which was derived from the ninth entry on Table 2, above. It had a chemical formula of $Nb_{2.0}W_{2.8}N_{5.1}O_{4.5}$. It had the following physical properties:

---
$S_A = 72.4 \text{ m}^2/\text{g}$
CO up-take > 2.2 μmol/g
Elemental analysis: (Wt %)
    Nb  W  N  (O)
    22  61  8.5  8.5
Chemical formula: $Nb_{2.0}W_{2.8}N_{5.1}O_{4.5}$
Lattice parameter (fcc): a = 4.18
β-$W_2N$ (fcc) :a = 4.12
δ$NbN_x$ (fcc):  a = 4.38  a = 4.37  a = 4.37
           (x = 0.86)  (x = 1.00)  (x = 1.06)
a(β-$W_2N$) < a(Nb-W-1) < a(δ-$NbN_x$)

---

The following results were obtained in catalytic testing, similar to those in Example 44:

| Reaction Temp (°C.) | Conversion (%) | Selectivity | | |
|---|---|---|---|---|
| | | $C_6$-$C_7$ Isomers (%) | $C_1$-$C_6$ Hydrocarbons (%) | Aromatics (%) |
| 330 | 5 | 87.6 | 9.0 | 1.6 |
| 350 | 9 | 78.7 | 12.0 | 3.8 |
| 450 | 26 | 22.4 | 23.7 | 49.8 |

Conversion to $C_6$ and $C_7$ isomers and to aromatics was also achieved.

EXAMPLE 45

The same procedure used in Example 43 was used with a niobium-molybdenum nitride-oxynitride catalyst (the third entry on Table 2, above). The following results were obtained in catalytic testing similar to those in Example 44:

| Reaction Temp (°C.) | Conversion (%) | Selectivity | | |
|---|---|---|---|---|
| | | $C_6$-$C_7$ Isomers (%) | $C_1$-$C_6$ Hydrocarbons (%) | Aromatics (%) |
| 350 | 15 | 43 | 53 | 4 |
| 400 | 25 | 20 | 60 | 20 |

EXAMPLE 46

The same procedure employed in Examples 43 and 45 was used with a tungsten-molybdenum nitride-oxynitride catalyst (the tenth entry in Table 2, above):

| Reaction Temp (°C.) | Conversion (%) | Selectivity | | |
|---|---|---|---|---|
| | | $C_6$-$C_7$ Isomers (%) | $C_1$-$C_6$ Hydrocarbons (%) | Aromatics (%) |
| 350 | 20 | 50 | 47 | 3 |

The foregoing Examples, since they merely illustrate certain preferred embodiments of the claimed invention should not be construed in a limiting sense. The scope of protection sought is set forth in the claims which follow.

We claim:

1. An oxynitride comprising two differing transition metals.
2. An oxynitride as claimed in claim 1 wherein at least one transition metal is selected from the group consisting of molybdenum and tungsten.
3. An oxynitride as claimed in claim 2 wherein the other transition metal is selected from the group consisting of chromium and another transition metal which is selected from the group consisting of Groups IIIB to VB and VIIB to VIII of the Periodic Table of the Elements.
4. An oxynitride as claimed in claim 2 wherein molybdenum is one transition metal and the other transition metal is selected from the group consisting of yttrium, vanadium, niobium, chromium, manganese, cobalt, and nickel.
5. An oxynitride as claimed in claim 2 wherein tungsten is one transition metal and the other transition metal is selected from the group consisting of vanadium, niobium, and cobalt.
6. Yttrium molybdenum oxynitride.
7. Vanadium molybdenum oxynitride.
8. Niobium molybdenum oxynitride.
9. Chromium molybdenum oxynitride.
10. Manganese molybdenum oxynitride.
11. Cobalt molybdenum oxynitride.
12. Nickel molybdenum oxynitride.
13. Vanadium tungsten oxynitride.
14. Niobium tungsten oxynitride.
15. Molybdenum tungsten oxynitride.
16. Cobalt tungsten oxynitride.
17. A nitride comprising two differing transition metals in a face centered cubic arrangement and having a surface area of no less than about 40 $m^2$/gm.
18. A nitride as claimed in claim 17 wherein at least one transition metal is selected from the group consisting of molybdenum and tungsten.
19. A nitride as claimed in claim 18 wherein the other transition metal is selected from the group consisting of chromium and another transition metal which is selected from the group consisting of Groups IIIB to VB and VIIB to VIII of the Periodic Table of the Elements.
20. A nitride as claimed in claim 18 wherein molybdenum is one transition metal and the other transition metal is selected from the group consisting of yttrium, vanadium, niobium, chromium, manganese, cobalt, and nickel.
21. A nitride as claimed in claim 18 wherein tungsten is one transition metal and the other transition metal is selected from the group consisting of vanadium, niobium, and cobalt.
22. A hydrotreating process comprising contacting a hydrocarbon feedstock at elevated temperature and under pressure with a catalyst as claimed in claim 1.
23. A hydrotreating process comprising contacting a hydrocarbon feedstock at elevated temperature and under pressure with a catalyst as claimed in claim 17.
24. A hydroisomerization process comprising contacting a hydrocarbon feedstock at elevated temperature and under pressure with a catalyst as claimed in claim 1.
25. A hydroisomerization process comprising contacting a hydrocarbon feedstock at elevated temperature and under pressure with a catalyst as claimed in claim 17.

* * * * *